US00PP28553P3

(12) United States Plant Patent
Werner

(10) Patent No.: US PP28,553 P3
(45) Date of Patent: Oct. 24, 2017

(54) ***BUDDLEJA* PLANT NAMED 'MISS PEARL'**

(50) Latin Name: ***Buddleja* sp.**
Varietal Denomination: MISS PEARL

(71) Applicant: Dennis James Werner, Raleigh, NC (US)

(72) Inventor: Dennis James Werner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 153 days.

(21) Appl. No.: 14/756,094

(22) Filed: Jul. 31, 2015

(65) Prior Publication Data

US 2017/0006754 P1 Jan. 5, 2017

(51) Int. Cl.
*A01H 5/00* (2006.01)

(52) U.S. Cl.
USPC ..... Plt./242

(58) Field of Classification Search
USPC ..... Plt./226, 242
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Buddleja* cultivar named 'MISS PEARL' is disclosed, characterized by white ruffled flowers, upright spike-like inflorescences, compact growth habit with high lateral branching and dense foliage, medium green leaf color (adaxial side) with silver-gray underside. Plants are female sterile and anthers malformed or lacking. The new variety is a *Buddleja*, normally produced as an outdoor garden or container plant.

3 Drawing Sheets

Latin name of the genus and species: *Buddleja* sp.
Variety denomination: 'MISS PEARL'.

BACKGROUND OF THE INVENTION

The new *Buddleja* cultivar is a product of a planned breeding program conducted by the inventor, Dennis James Werner, at a research greenhouse in Raleigh, N.C., U.S.A. The objective of the breeding program was to produce new *Buddleja* varieties for ornamental commercial applications. The cross resulting in this new variety was made during July of 2009.

The seed parent is the, patented, commercial variety referred to as *Buddleja* 'Ice Chip' U.S. Plant Pat. No. 24,015. The pollen parent is the patented, commercial variety referred to as *Buddleja* 'Miss Molly' U.S. Plant Pat. No. 23,425 The new variety was discovered on Jun. 21, 2011 by the inventor in a group of seedlings resulting from the 2009 crossing, at a research nursery in Jackson Springs, N.C., U.S.A.

Asexual reproduction of the new cultivar was performed by semi-hardwood stem cuttings. This was first performed at the Horticulture Field Lab greenhouse NCSU Raleigh, N.C., U.S.A. in July of 2015 and has shown that the unique features of this cultivar are stable and reproduced true to type in 2 successive generations.

SUMMARY OF THE INVENTION

The cultivar 'MISS PEARL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MISS PEARL' These characteristics in combination distinguish 'MISS PEARL' as a new and distinct *Buddleja* cultivar:

1. Whited flowers with ruffled petals.
2. Upright, spike-like inflorescences.
3. Compact growth habit with high lateral branching and dense foliage.
4. Medium green leaf color (adaxial side) with silver-gray underside.
5. Essentially female sterile.
6. Anthers malformed or lacking.

Plants of the new cultivar 'MISS PEARL' are similar to plants of the seed parent, *Buddleja* 'Ice Chip' U.S. Plant Pat. No. 24,015 in most horticultural characteristics, however, plants of the new cultivar 'MISS PEARL' differ in the following;

1. Semi-upright growth habit, whereas the seed parent has a spreading growth habit.
2. Ruffled petals, whereas the seed parent has non-ruffled petals.
3. The new variety produces more flowers.
4. The new variety is less vigorous.

Plants of the new cultivar 'MISS PEARL' are similar to plants of the pollen parent, *Buddleja* 'Miss Milly' U.S. Plant Pat. No. 23,425 in most horticultural characteristics, however, plants of the new cultivar 'MISS PEARL' differ in the following;

1. Flowers color is white, whereas the pollen parent has deep pink flowers.
2. Essentially female sterile, whereas the pollen parent is moderately female fertile.

COMMERCIAL COMPARISON

Plants of the new cultivar 'MISS PEARL' are comparable to the unpatented commercial variety *Buddleja* 'White Ball'.

The two *Buddleja* varieties are similar in most horticultural characteristics; however, the new variety 'MISS PEARL' differs in the following:

1. Semi-upright growth habit whereas the comparator has a rounded growth habit.
2. Longer inflorescences.
3. Taller stature.
4. Ruffled petals, whereas the comparator has non-ruffled petals.

Plants of the new cultivar 'MISS PEARL' can also be compared to the patented commercial variety *Buddleja* 'Miss Ruby' U.S. Plant Pat. No. 19,950. The two *Buddleja* varieties are similar in most horticultural characteristics; however, the new variety 'MISS PEARL' differs in the following:

1. Flower color is white whereas the comparator flower color is pink.

BRIEF DESCRIPTION OF THE PHOTOGRAPHS

The accompanying photograph in FIG. 1 illustrates in full color a typical inflorescence of 'MISS PEARL'.

Figure 1:
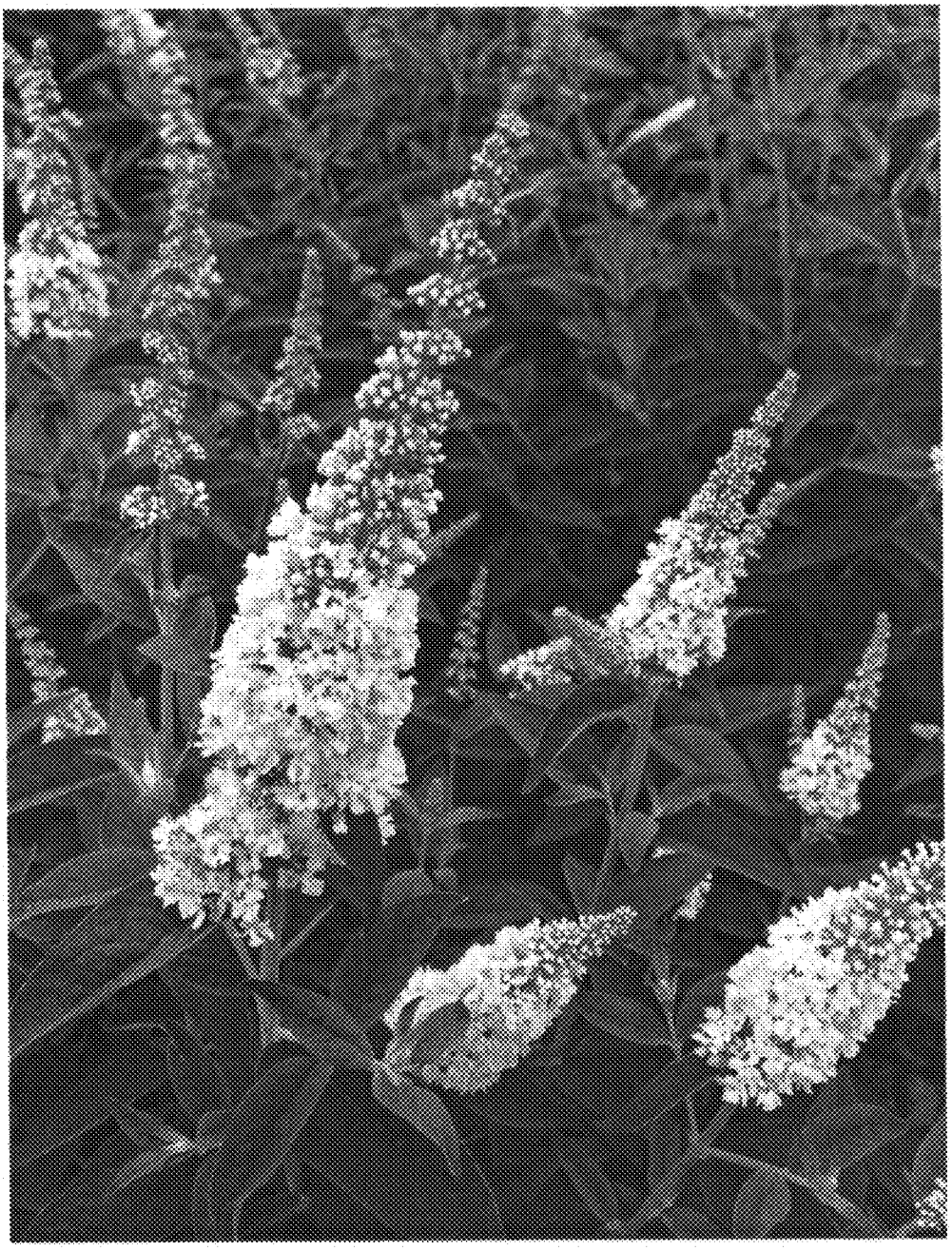
Figure 2:
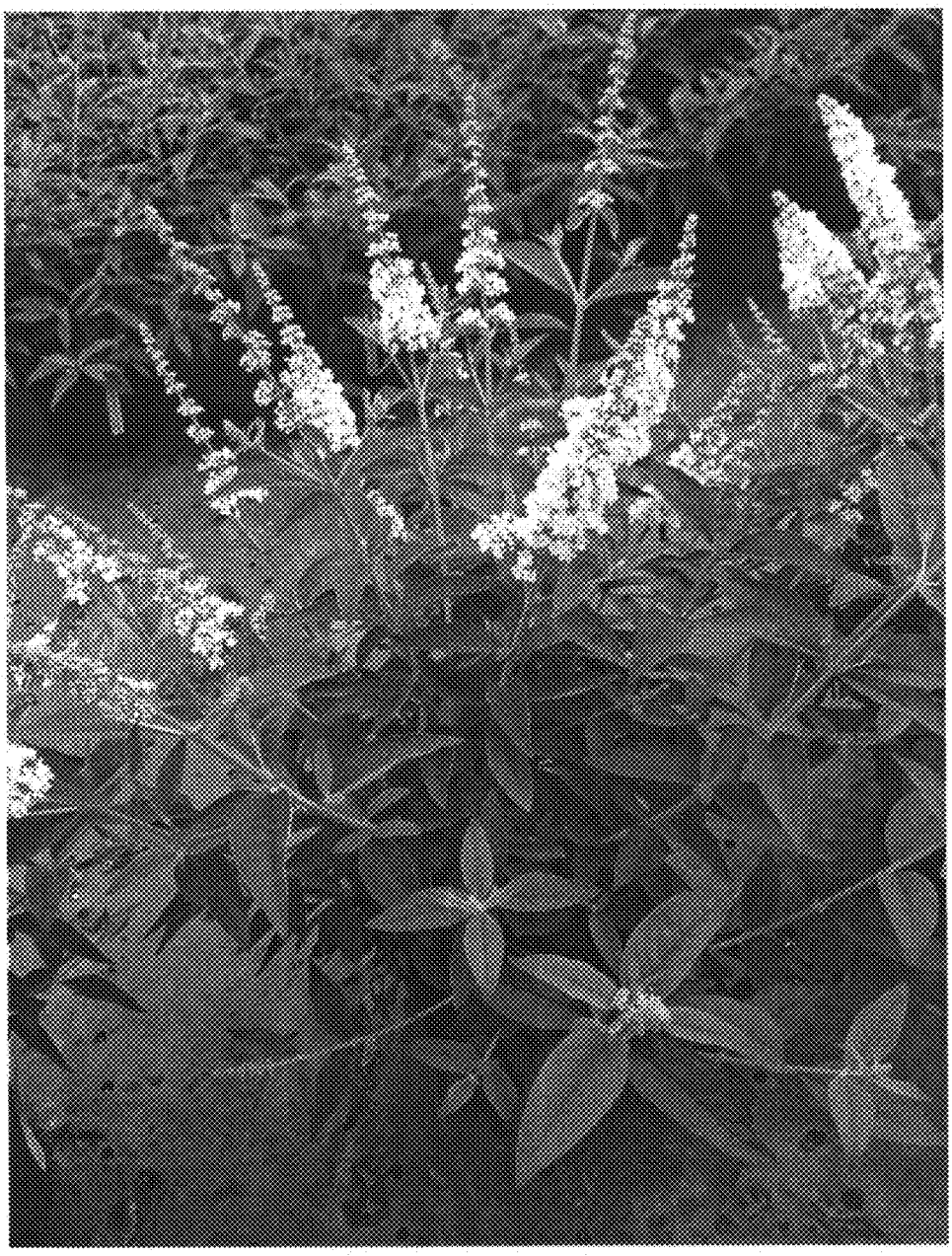
FIG. 2 illustrates a plant of 'Miss Pearl' grown in a nursery, in a 3 gallon pot. Age of the plant photographed is approximately 2-3 years old from a rooted cutting.
Figure 3:
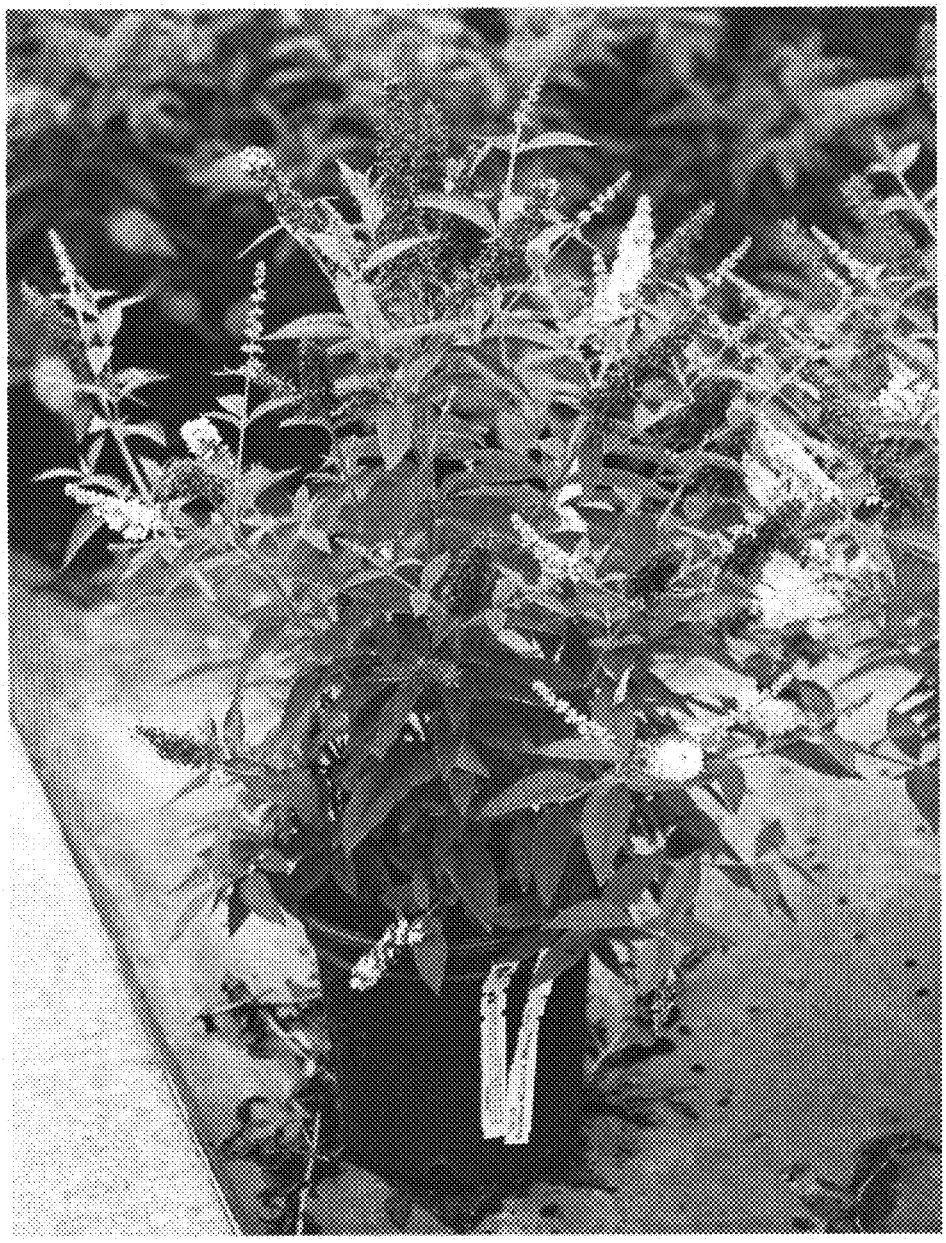
FIG. 3 illustrates a plant of 'Miss Pearl' grown in a nursery, in a 1 gallon pot, with aging inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'MISS PEARL' plants grown in a poly greenhouse during the June, in Grand Haven, Mich. U.S.A. The growing temperature ranged from 18° C. to 27° C. during the day and from 5° C. to 10° C. during the night. General light conditions are bright, normal sunlight. Measurements and numerical values represent averages of typical plant types.

Botanical classification: *Buddleja* 'MISS PEARL'.

PROPAGATION

Type of propagation typically used: Softwood or semi-hardwood cutting.

Time to initiate roots: 14-21 days at 21-23.8° C. average temperature.

Time to produce a rooted young plant: 45 days at 21-23.8° C. average temperature.

Root description: Dense, free-branching, medium thickness, fleshy. Color is tan, not accurately described with R.H.S. chart.

PLANT

Age of plant described: 1 year from rooted cutting.

Plant type: Perennial shrub.

Container size of the plant described: 3 gallon pot.

Appropriate containers: 1, 2, 3, 5 gallon commercial pots.

Growth habit: Upright.

Overall plant shape: Irregular cylindric.

Height: 63-76 cm in a 3 gallon container.

Plant spread: 63-76 cm in a 3 gallon container.

Growth rate: Moderate.

Plant vigor: Moderate.

Characteristics of primary lateral branches:

- *Quantity*.—Average 50.
- *Branching habit*.—Upright, basal branching some pinching required.
- *Branch appearance*.—Square.
- *Length*.—10-12 in.
- *Diameter*.—3 mm.
- *Color*.—RHS Yellow-green 144A.
- *Pubescence*.—Highly pubescent.
- *Stem aspect/angle*.—Angle can be between 45° to 90° from center of plant.
- *Strength*.—Moderate.

Internode length: 7 cm.

FOLIAGE

Leaf:

- *Arrangement*.—Opposite, single.
- *Average length*.—9-10 cm.
- *Average width*.—4.5 cm.
- *Shape*.—Lanceolate.
- *Apex*.—Acute.
- *Base*.—Cuneate.
- *Margin*.—Slightly undulate and serrate.
- *Texture of top surface*.—Soft/pubescent.
- *Texture of bottom surface*.—Soft/pubescent.
- *Pubescence*.—Yes, both upper and lower side of leaf.
- *Color*.—Young foliage upper side: RHS Green 139A. Young foliage under side; Near RHS Greyed-green 191B. Mature foliage upper side: RHS Green 139A. Mature foliage under side: Near RHS Greyed-green 191B.
- *Venation*.—Type: Pinnate. Venation color upper side: RHS Green 139A. Venation color under side: Near RHS Greyed-green 191B.
- *Petiole*.—Length: 3 mm. Diameter: 2 mm. Color: Upper side: Near RHS Greyed-green 191B. Lower side: Near RHS Greyed-green 191B. Texture: Upper side: Soft/pubescent. Lower side: Soft/pubescent.

FLOWER

Flower arrangement: Cone shape panicle.

Flower type: Slaverform.

Flowering habit: Paniculate.

Natural flowering season: Late Spring to early Summer in greenhouse early to late Summer in landscape.

Inflorescence height: 4 cm.

Inflorescence width: 2.5 cm.

Inflorescence and flower type and habit: Dense panicle, terminal and axillary.

Rate of flower opening: Moderate.

Flower longevity on plant: 3-4 weeks.

Persistent or self-cleaning: Self-cleaning.

Quantity of flowers per inflorescence: Approximate average of 200.

Quantity of flowers per plant: Approximately 10,000 on 50 blooming inflorescence.

Bud:

- *Shape*.—Elongated, linear balloon.
- *Length*.—3 mm.
- *Diameter*.—1-2 mm.
- *Color*.—RHS Yellow-white 158D.

Flower size:
*Diameter.*—3 mm.
*Length.*—5 mm.
*Depth (height).*—5 mm.
Petals:
*Appearance.*—Smooth, white, ruffled.
*Arrangement.*—Whorled, fused.
*Petal length.*—4 mm.
*Petal width.*—3 mm.
*Quantity.*—5.
*Texture.*—Smooth and soft.
*Apex.*—Obtuse.
*Shape.*—Rotund.
*Base.*—Acute.
*Margin.*—Undulate.
*Aspect.*—Upright/outward.
Petal color:
*When opening.*—Upper surface: RHS White 155A. Lower surface: RHS White 155A.
*Fully opened.*—Upper surface: RHS White 155C. Lower surface: RHS White 155C.
*Fading to color.*—Upper and lower: RHS Greyed-yellow 160D fading to Greyed-orange 165B.
Sepals:
*Quantity per flower.*—5.
*Arrangement.*—Whorled.
*Shape.*—Lanceolate to Ovate.
*Length.*—3 mm.
*Width.*—2 mm.
*Apex.*—Acute.
*Base.*—Cuneate.
*Margin.*—Entire/inconspicuous.
*Texture.*—Upper: Smooth/pubescent. Lower: Smooth/slightly pubescent.
*Color.*—Upper Surface: RHS Yellow-green 144A. Lower Surface: RHS Yellow-green 144A.
Calyx:
*Shape.*—Oblong and unguiculate.
*Length.*—1 mm.
*Diameter.*—1 mm.
*Color.*—Too minute to accurately measure.
Peduncle:
*Length.*—1 mm.
*Diameter.*—0.5 mm.
*Angle.*—Upright/outward.
*Strength.*—Moderate.
*Texture.*—Smooth/pubescent.
*Color.*—RHS Greyed-orange 168D.
Pedicel: Not present.
Fragrance: Moderate; sweet fragrance.

REPRODUCTIVE ORGANS

Stamens:
*Number.*—4.
*Filament length.*—0.5 mm.
*Filament color.*—RHS yellow-green 145A.
Anthers:
*Shape.*—Malformed, less than 1 mm.
*Pollen.*—Quantity: Scant.
Pistil:
*Number.*—1.
*Length.*—3 mm.
*Style.*—Length: 1.5 mm. Color: RHS Yellow-green 144D.
*Stigma.*—Shape: Round. Color: RHS Yellow-green 144C. Ovary Color: RHS Yellow-green 144C.

OTHER CHARACTERISTICS

Seeds and fruits: Not observed to date.
Disease/pest resistance: Neither resistance nor susceptibility to the normal diseases and pests of *Buddleja* observed to date.
Lowest temperature tolerance: To date in trials −13.9° C.
Highest temperature tolerance: To date in trials 38.8° C.
Garden performance: Good to excellent.

What is claimed is:

1. A new and distinct cultivar of *Buddleja* plant named 'MISS PEARL' as herein illustrated and described.

* * * * *